(12) United States Patent
Shampine et al.

(10) Patent No.: US 7,639,781 B2
(45) Date of Patent: *Dec. 29, 2009

(54) X-RAY TOOL FOR AN OILFIELD FLUID

(75) Inventors: Rod Shampine, Houston, TX (US); Joel L. Groves, Leonia, NJ (US); Anthony Durkowski, Lawrenceville, NJ (US); Etienne Vallee, Princeton, NJ (US); Peter Wraight, Skillman, NJ (US)

(73) Assignee: Schlumberger Technology Corporation, Sugar Land, TX (US)

(*) Notice: Subject to any disclaimer, the term of this patent is extended or adjusted under 35 U.S.C. 154(b) by 56 days.

This patent is subject to a terminal disclaimer.

(21) Appl. No.: 12/016,330

(22) Filed: Jan. 18, 2008

(65) Prior Publication Data

US 2008/0152080 A1 Jun. 26, 2008

Related U.S. Application Data

(63) Continuation-in-part of application No. 11/532,236, filed on Sep. 15, 2006, which is a continuation-in-part of application No. 11/751,727, filed on May 22, 2007, now abandoned.

(51) Int. Cl.
*G01B 15/02* (2006.01)
*H01J 35/08* (2006.01)
*G21K 1/02* (2006.01)
*G01V 5/12* (2006.01)

(52) U.S. Cl. .................. 378/54; 378/143; 378/147; 250/258; 250/269.1

(58) Field of Classification Search ............ 378/51–54, 378/56; 250/253–258, 261, 268, 269.1, 362, 250/370.06

See application file for complete search history.

(56) References Cited

U.S. PATENT DOCUMENTS

| | | | | |
|---|---|---|---|---|
| 4,125,769 | A * | 11/1978 | Marten et al. | 378/47 |
| 4,228,353 | A * | 10/1980 | Johnson | 250/356.1 |
| 4,355,410 | A * | 10/1982 | Sullins | 378/199 |
| 4,885,759 | A * | 12/1989 | Tomoda et al. | 378/53 |
| 5,441,340 | A | 8/1995 | Cedillo et al. | |
| 5,479,020 | A * | 12/1995 | Mohn | 250/356.1 |
| 5,689,540 | A * | 11/1997 | Stephenson et al. | 378/53 |
| 5,822,390 | A * | 10/1998 | Hewitt et al. | 378/53 |
| 6,097,786 | A * | 8/2000 | Groves et al. | 378/53 |
| 6,265,713 | B1 * | 7/2001 | Berard et al. | 250/269.3 |
| 6,389,908 | B1 * | 5/2002 | Chevalier et al. | 73/861.63 |

(Continued)

*Primary Examiner*—Edward J Glick
*Assistant Examiner*—Anastasia Midkiff
(74) *Attorney, Agent, or Firm*—Michael Flynn; David Cate; Robin Nava (57) ABSTRACT

An x-ray tool for determining a characteristic of an oilfield fluid. The tool may include a generator portion housing a collimator about a target from which x-rays are emitted. In this manner x-rays may be attenuated right at the target such that a majority of shielding otherwise necessary for safety concerns may be eliminated. Rather, by employing the target within the collimator, shielding of the generator may be limited to a single shielding plate within the generator portion that is positioned parallel to the target at the opposite end of an x-ray tube therebetween. As a result of this configuration, an x-ray tool for analysis of oilfield fluids may be provided with a minimum weight of shielding material. Thus, hand-held user friendly embodiments may be safely employed at the oilfield.

28 Claims, 5 Drawing Sheets

U.S. PATENT DOCUMENTS

| | | |
|---|---|---|
| 6,412,561 B1 | 7/2002 | Brown et al. |
| 6,722,437 B2 | 4/2004 | Vercaemer et al. |
| 6,776,235 B1 | 8/2004 | England |
| 7,162,005 B2 * | 1/2007 | Bjorkholm .................. 378/57 |
| 7,295,706 B2 * | 11/2007 | Wentland et al. ............ 382/181 |
| 2004/0173016 A1 * | 9/2004 | Fayeulle et al. .......... 73/152.31 |
| 2006/0203961 A1 * | 9/2006 | Morton ........................ 378/57 |
| 2008/0069301 A1 * | 3/2008 | Shampine et al. ............. 378/53 |

* cited by examiner

X-RAY TOOL FOR AN OILFIELD FLUID

PRIORITY CLAIM

This Patent Document is a Continuation-In-Part of application Ser. No. 11/532,236, Apparatus and Method for Well Services Fluid Evaluation Using X-Rays, filed Sep. 15, 2006. This Patent Document is also a Continuation-In-Part of application Ser. No. 11/751,727, X-Ray Tool For An Oilfield Fluid, filed May 22, 2007 now abandoned.

BACKGROUND

Embodiments described relate to tools for aiding in analysis of fluids at an oilfield. In particular, embodiments of x-ray tools that are compact and highly mobile are described.

BACKGROUND OF THE RELATED ART

The production of hydrocarbons from an oilfield generally involves a variety of applications employing oilfield fluids. For example, a host of large scale equipment may be delivered to an oilfield for the purpose of extracting hydrocarbons therefrom. These applications may involve the addition of oilfield fluids through a well drilled into a formation at the oilfield in order to provide access to the hydrocarbons. The hydrocarbons may then be extracted from the well along with, in some cases, the added oilfield fluids.

One application involving the addition of an oilfield fluid is a drilling application employed to initially form the well wherein a drilling mud is circulated to and from a bit during drilling. Another application of an oilfield fluid may include a well completion application in order to provide structural integrity and manageability to the well. Such well completion applications may involve the cementing of borehole casing sections within the well whereby cement is pumped into the well and forced between the borehole casing sections and an otherwise exposed wall of the well.

Other fluids may be introduced to the well in addition to mud and cement. For example, a fracturing fluid may be introduced to a well under high pressure in order to form fractures through the wall of the well and into the formation at a production region thereof. A certain percentage of the fracturing fluid may also be retrieved from the well thereafter. Similarly, dosing and other applications may involve the addition of an oilfield fluid to the well.

The particular characteristics of an oilfield fluid such as those described above may be critical to the effectiveness of the application making use of the oilfield fluid. Therefore, attempts to closely monitor the characteristics of oilfield fluids during use are quite common. For example, in the case of a fracturing application, the density of fracturing fluid injected into the well is often monitored as it is injected. The density of the fracturing fluid may provide information as to the amount of proppant that is provided to the well during the procedure. This may be very important information, when considering that the type and amount of proppant are generally key factors to the formation of fractures as described above. In fact, in many circumstances, the fracturing fluid is actually charged to the user based on the amount of proppant that is pumped downhole into the well during the application. Therefore, the accuracy of the described density monitoring may be of great importance. This is especially true when in light of the fact that a typical fracturing application may involve between about ½ and about 2 million pounds of proppant. As a result, accuracy to within one percent is generally required as industry standard for density monitoring of fracturing fluids.

In order to accurately monitor the density of fracturing fluid as it is pumped into the well, a variety of radioactive densitometers are often employed at the oilfield. A radioactive densitometer may be coupled about a line leading from a fracturing pump assembly or manifold and to the well. The densitometer includes a radioactive source such as radioactive cesium (generally $Cs^{137}$) positioned at one location of the line. A detector is positioned at the opposite side of the line for detection of the gamma rays emitted by the cesium. The density of fracturing fluid within the line, in addition to the material of the line itself, will determine what is ultimately detected by the detector. Thus, once accounting for the line material, a comparison of the amount of gamma rays emitted from the source with the amount detected by the detector will provide information indicative of the density of the fracturing fluid flowing within the line. Radioactive densitometers employed in this manner are generally accurate to within about one percent.

Unfortunately, radioactive densitometers as described above involve the use of hazardous radioactive material on site. The densitometers must be manually positioned and employed in a hands-on manner subjecting users to significant risk of exposure to dangerous levels of radiation. In order to account for the inherent risks of employing radioactive material at the operation site, the densitometer is generally provided as part of a massive assembly that is made up primarily of shielding material. As a result, the mobility of the radioactive densitometer assembly is substantially compromised. Furthermore, there remains the possibility of failure of a portion of the shielding which, even if only to a minimal degree, may pose very significant health risks to anyone on site.

In order to address concerns over the hazards of employing radioactive sources, a photon generator in the form of an x-ray densitometer may be employed as detailed in application Ser. No. 11/532,236, Apparatus and Method for Well Services Fluid Evaluation Using X-Rays, filed Sep. 15, 2006. In this manner, x-rays may be transmitted through the line for detection by a detector similar to the radioactive densitometer described above. Yet, in the case of an x-ray densitometer, the emitted x-rays would be powerful enough for complete transmission through the line but at a significantly lower energy level than the gamma rays that are transmitted by the radioactive densitometer. Furthermore, when not in use, the x-ray densitometer may simply be turned off, leaving no significant concern over hazardous emissions.

The above described advantages of an x-ray densitometer may be quite significant, especially considering the complete elimination of a hazardous radioactive source on site. Nevertheless, during operation the x-ray densitometer may emit a significant amount of lower energy, but still potentially hazardous x-rays. Therefore, a substantial amount of shielding remains necessary in order to ensure the complete safety of nearby users. As a result, the x-ray densitometer remains a fairly immobile, 150 to 250 pound, assembly. Thus, set-up, positioning, and take down of the assembly on site remains a significant challenge to the user.

SUMMARY

An x-ray tool for determining a characteristic of an oilfield fluid is provided. The x-ray tool may include a generator that provides an electron beam to a target coupled to an x-ray tube, the target for receiving the electron beam and emitting x-rays in response thereto. A collimator may be provided about the target for collimating the x-rays.

DETAILED DESCRIPTION

Embodiments are described with reference to certain x-ray tools for use in fracturing applications at an oilfield. However, other oilfield applications may make use of x-ray tool embodiments described herein. For example, cementing and drilling applications may employ embodiments of x-ray tools described herein. Regardless, embodiments described include x-ray tools that require no more than about 25 lbs. or less of shielding in order to be safely employed by a user. In fact, oilfield x-ray tools described below may be less than about 50 lbs. in total weight and of mobile configurations for hand-held user-friendly handling and placement at the oilfield.

Figure 1:
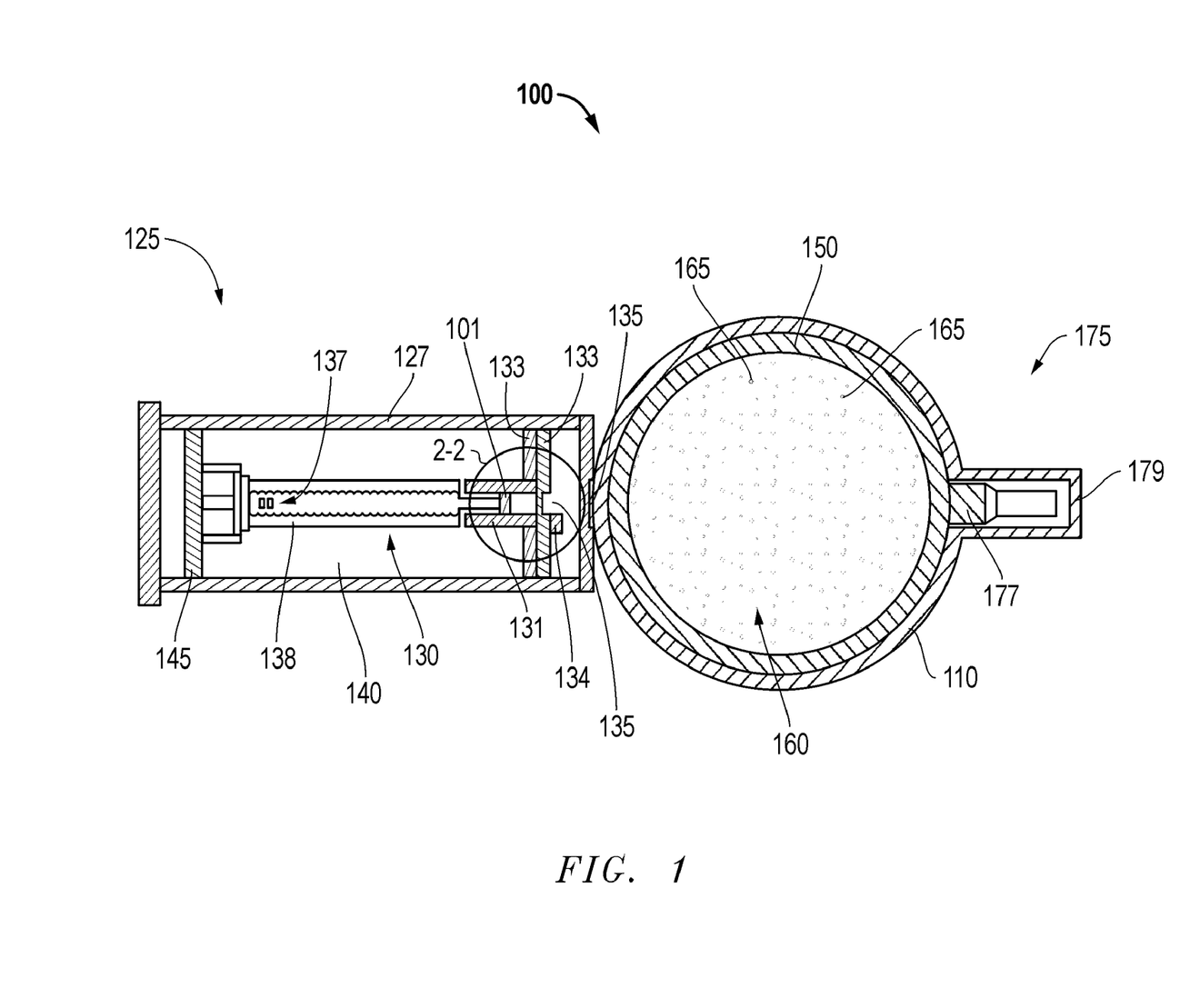
FIG. 1 is a side cross-sectional view of an embodiment of an oilfield x-ray tool coupled to an oilfield fluid line.
Figure 3:
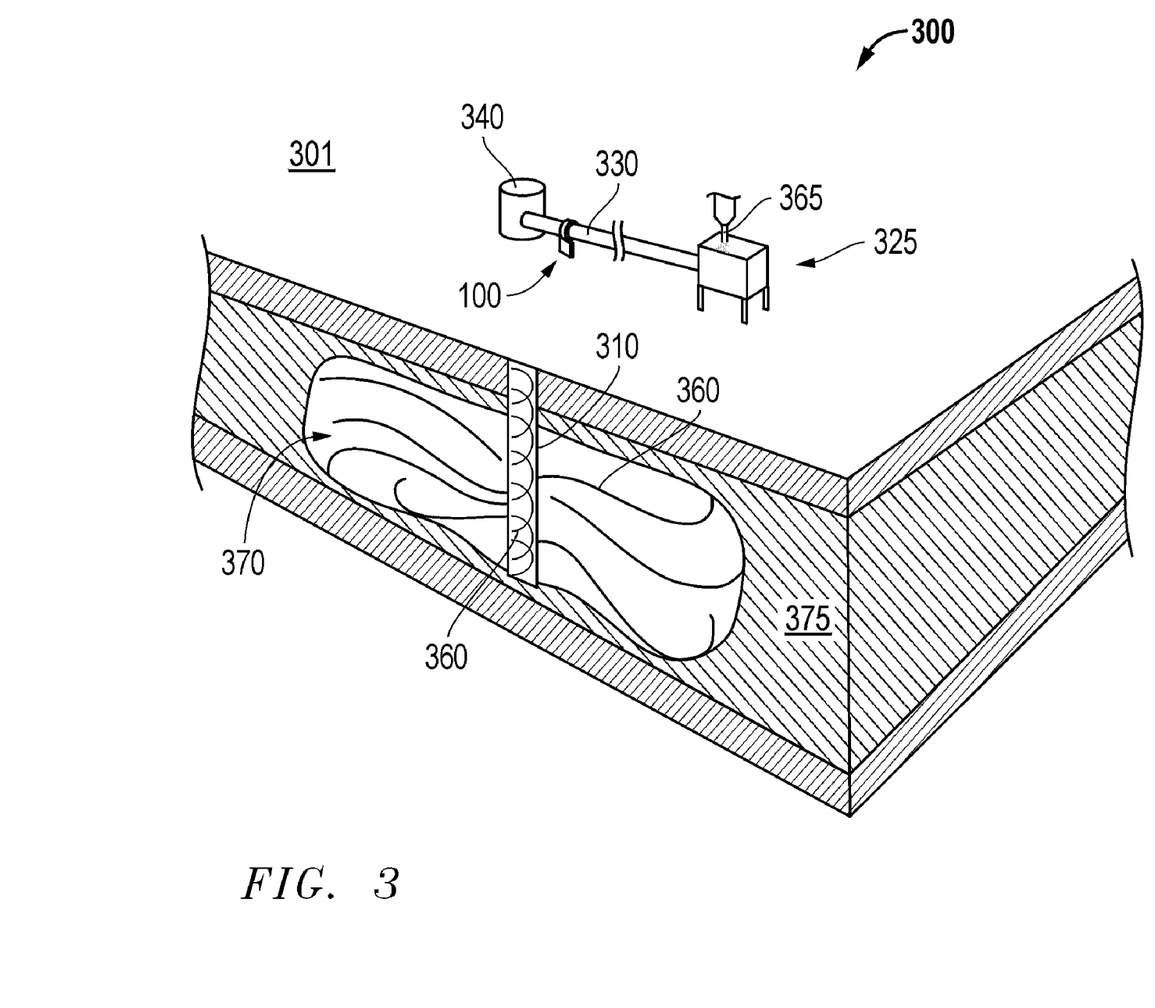
FIG. 3 is an overview of an oilfield operation employing the oilfield x-ray tool of FIG. 1.

Referring now to FIG. 1 an embodiment of an oilfield x-ray tool 100 is depicted coupled to an oilfield fluid line 150. The oilfield fluid line 150 is configured to transport an oilfield fluid 160 to a well 310 at an oilfield 301 as shown in FIG. 3. In particular, the embodiment shown reveals an oilfield fluid 160 in the form of a fracturing fluid for a fracturing application. A proppant 165 is disbursed through the fluid 160 to aid in the high pressure fracturing of a geologic formation. In other embodiments, however, other types of oilfield fluids and applications may be employed, including a cement slurry for cementing or a drilling mud for drilling.

The oilfield x-ray tool 100 of FIG. 1 is configured to help determine information as to characteristics of the oilfield fluid 160 in the line 150. Such information may relate to density, solid fraction, solid, liquid and gas phase or physical state characteristics, material composition or other properties. Furthermore, even with more than adequate x-ray shielding being integrated therein, the tool 100 may be a hand-held, manually positioned, user-friendly device of less than about 50 lbs. and preferably less than about 30 lbs. in total weight.

Figure 2:
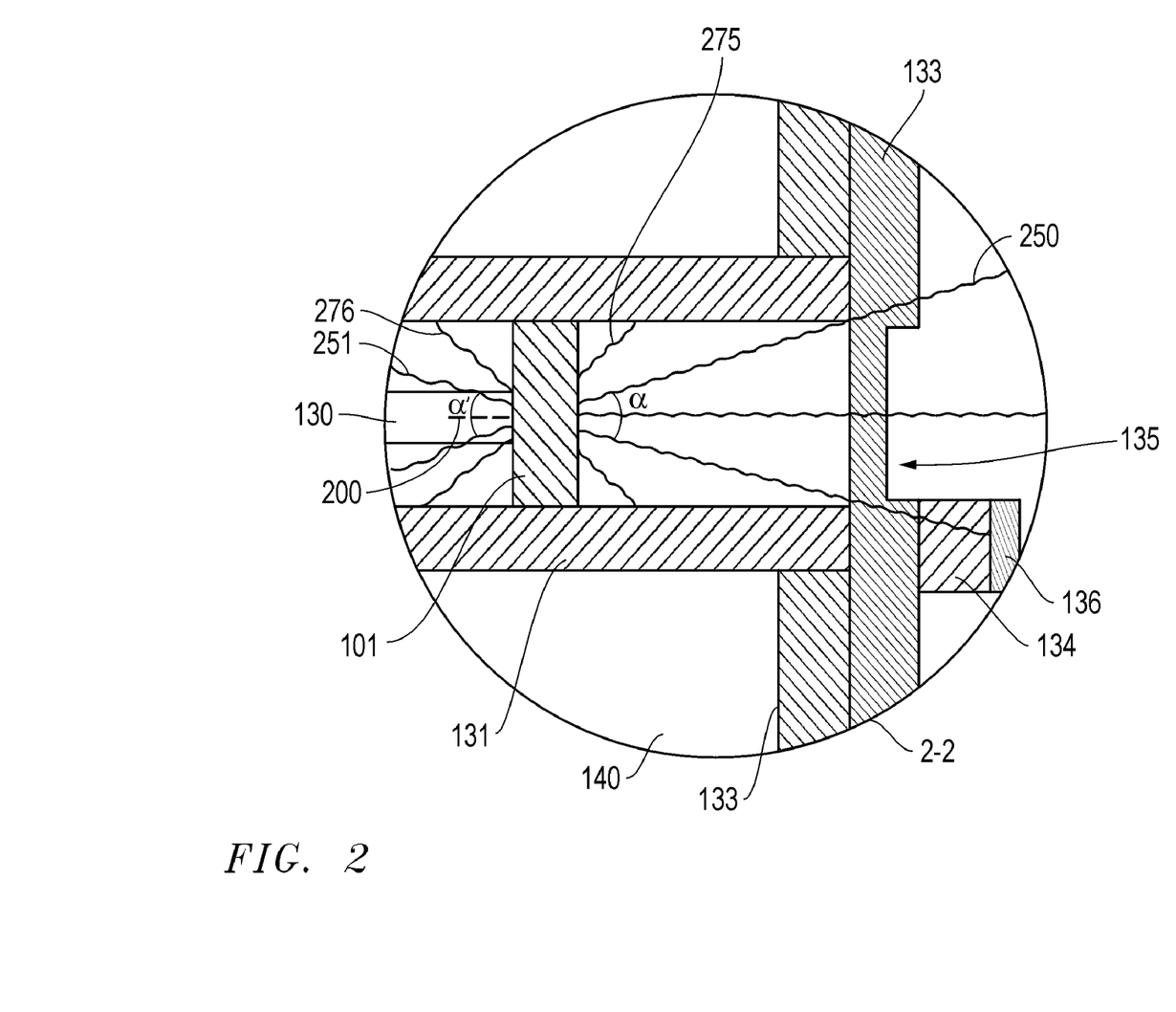
FIG. 2 is an enlarged view of a portion of the oilfield x-ray tool of FIG. 1 taken from section line 2-2.

With added reference to FIG. 2, the oilfield x-ray tool 100 is shown with a generator portion 125 coupled to a detector portion 175 through a clamp or cuff 110 about the oilfield fluid line 150. The cuff 110 is sized such that outlets 135 of the generator portion 125 are in alignment with a detection mechanism 177 of the detector portion 175. In one embodiment the detection mechanism 177 is of a scintillating material interfaced with a photocathode and electron multiplier in order to achieve the indicated detection. As detailed further herein, x-rays 250 emitted by the generator portion 125 may be directed across the fluid line 150, attenuated to a degree by the oilfield fluid 160, and then detected by the detection mechanism 177. In this manner attenuation of the x-rays 250 by the oilfield fluid 160 may be discerned in order to provide information as to characteristics of the traversed oilfield fluid 160. In one embodiment, the detection mechanism 177 may be collimated to avoid detection of low level scattered x-rays that may indirectly traverse the oilfield fluid 160 on occasion. Such x-rays may be fairly harmless, yet primarily uninformative and potentially even a hindrance to effective and accurate determination of oilfield fluid characteristics.

The indicated fluid line 150 may be a steel pipe with a pressure rating of at 15,000 lbs/in$^2$. or greater with about ½ inch thick walls. Thus, the x-ray tool 100 may be of a configuration generating x-rays at energies up to 400 keV in order to effectively traverse the fluid line 150 as indicated. While the maximum x-ray energy is still significantly less than the gamma-ray energies emitted by radioactive sources typically used as described above, a degree of shielding 145 may still be provided as detailed below.

Continuing with reference to FIG. 1, again with added reference to FIG. 2, the generator portion 125 is configured to direct an electron beam 200 at a target 101 in order to generate x-rays 250 through the fluid line 150 as indicated above. In the embodiment shown, the generator portion 125 may include a conventional cathode that emits electrons when heated by an electric current and thereby release electrons. The cathode 137 may be coupled to or disposed within an x-ray tube 130. The x-ray tube consists of a cathode section 137, an insulating electron acceleration section 138 and a target section 101. The electron acceleration section 138 may be of any insulating material able to maintain the high voltage difference between the target and the cathode; typically glass or ceramic materials are used for the electron acceleration section. The target 101 may be of gold, copper, or other suitable material and of sufficient thickness to stop the electron beam 200. However, in the process, the target 101 emits x-ray photons (e.g. 250).

The x-ray tube 130 may be disposed in a dielectric material space 140 that is filled with sulfur hexafluoride, transformer oil, or other suitably inert, preferably airless medium. Additionally, in the embodiment shown, the x-ray tube 130 is grounded near the target 101. However, in other embodiments the x-ray tube 130 may be grounded near the cathode 137. Furthermore, the x-ray tube 130 and other inner workings of the generator portion 125 are mounted within a rigid casing 127 that is directly coupled to the indicated cuff 110. The shielding 145 may be of lead, gold, tungsten or other appropriate material of a thickness sufficient to reduce the radiation dose at the surface of the casing to the desired level.

In the embodiment described here, the end of the x-ray tube 130 with the cathode 137 is at high voltage. By grounding the target end of the x-ray tube 130, the collimator 131 may be positioned directly adjacent the x-ray tube 130, closely surrounding it and being of limited size while providing the collimating benefits described in further detail below.

The target 101 end of the x-ray tube 130 is coupled to a collimator 131 which is in turn secured to support plates 133. The collimator 131 may be of lead, gold, copper, tungsten or other suitable shielding material and is often of the same material as the shielding 145. The support plates are secured to sidewalls of the rigid casing 127 thereby securely positioning the inner workings of the generator portion 125 in place. X-ray outlets 135 (windows) may be provided at the surface of the rigid casing 127 and the side plates 133. The outlets 135 may be thinned down areas of such supportive structures 127, 133 in order to allow a greater amount of x-rays 250 therethrough as depicted in FIG. 2.

A reference detector 134 may be coupled near the above noted outlets 135 in order to detect outgoing x-rays 250 in advance of traversing the fluid line 150 for comparison to x-rays detected at the opposite side of the fluid line 150 by the measurement detector 177. In one embodiment, the reference detector 134 is of substantially the same configuration as the measurement detector. Additionally, the reference detector 134 and the measurement detector 177 may be wired to a processor for analysis of data obtained therefrom. Furthermore, the measurement detector 177 itself may be housed within a rigid housing 179 that is coupled directly to the cuff 110 as noted above. The rigid housing 179 may also be configured to provide a support structure to the measurement detector portion 175 while also containing and shielding remaining x-rays directed thereat from the generator portion 125.

In the embodiments of FIGS. 1 and 2, the collimator 131 is provided about the target 101 inside the x-ray tube. That is, rather than placing the collimator around the outside of the x-ray tube, the collimator is actually disposed within the x-ray tube 131. In this manner, x-rays 250, 251, 275, 276 generated by the target 101 are immediately collimated such that the amount actually leaving the area of the collimator 101 are substantially limited to particular ranges of channeled x-rays 250, 251 to either side of the target 101 as defined by the angles α and α'. Blocked x-rays 275, 276 make up those falling outside of the ranges of angles α and α'. Such blocked x-rays 275, 276 are immediately shielded and substantially prevented from leaving the area of the collimator 131 altogether. In addition to the described x-rays 250, 251, 275, 276, a certain minimal degree of low level x-rays (not depicted) may scatter about the interior of the generator portion 125. However, the rigid casing 127 may be of a conventional stainless steel, thereby substantially eliminating the possibility of such low level x-rays leaving the generator portion 125 and posing a hazard to a user.

As a result of the above described collimator 131 and target 101 configuration, the amount of shielding required in order to render the x-ray tool 100 safe for manual use is drastically reduced. In fact, given that blocked x-rays 275, 276 emitted outside of the angles α and α' from the target 101 fail to leave the area of the collimator 131, only the channeled x-rays 250, 251 are of concern in terms of shielding. However, the channeled x-rays 250 of the angle α are intended to leave the generator portion 125 and travel toward the detector portion 175 as described above, naturally attenuating along the way. Therefore, the only remaining x-ray shielding safety concern is that relative to the channeled x-rays 251 of the angle α' back toward the source of the electron beam 200 described above (e.g. toward the cathode 137).

The channeled x-rays 251 of the angle α' may be adequately shielded by the provision of shielding 145 parallel to the target 101 such that the channeled x-rays 251 remain disposed between the target 101 and the shielding 145. Thus, the minimum dimensions of the shielding may be in direct correlation to the angle α' and the distance between the target 101 and the shielding 145.

Continuing with reference to FIG. 2, with added reference to FIG. 1, an enlarged portion of the x-ray tool 100 is depicted with view 2-2. In this view, the target end of the x-ray tube 130 contains collimator 131 adjacent the target 101. The collimator 131 cylindrically surrounds the target 101 for the noted collimating. In fact, given that the collimator 131 and the target 101 may be of the same material, in one embodiment the collimator 131 and the target 101 are actually of a unitary or monolithic configuration.

The electron beam 200 is shown traversing the x-ray tube 130 in FIG. 2 and striking the target 101 resulting in a spectrum of x-rays 250, 251, 275, 276 being emitted therefrom. The x-rays 250, 251, 275, 276 may be attenuated by the collimator 131 or channeled therefrom if falling within the proper angles α, α' as detailed above. These angles α, α' may be configured based on the dimensions of the collimator 131 and positioning of the target 101 therein. For example, in one embodiment the target 101 is positioned at about the midpoint of the collimator 131 with the angles α, α' being roughly equivalent and fairly narrow, at between about 1° and about 10°, depending on the length of the collimator 131. However, in other embodiments alternative ranges of angles α, α' may be employed for release of channeled x-rays 250, 251 from the collimator 131.

The channeled x-rays 250 exiting the collimator 131 toward the fluid line 150 may be pronounced through the shown outlet 135 where structural thickness is minimized. However, these same x-rays 250 may also reach a reference detector 134 to take a reading of x-rays 250 in advance of the fluid line 150 for comparison to x-ray detection obtained by the measurement detector 177 subsequent to x-ray traversing of the fluid line 150. In one embodiment, readings from the reference detector 134 may be used by a real-time feedback mechanism of a processor to tune the x-ray output of the tool 100. In another embodiment readings from the reference detector 134 and the measurement detector 177 may be comparatively analyzed at the processor. Additionally, data regarding known chemistries and other information relative to the potential types of fluid 160 may be stored in the processor. In this manner, a baseline of x-ray information may be established to determine the degree of x-ray attenuation within the fluid line 150. Thus, more accurate density or other information regarding the oilfield fluid 160 may be established.

Figure 4:
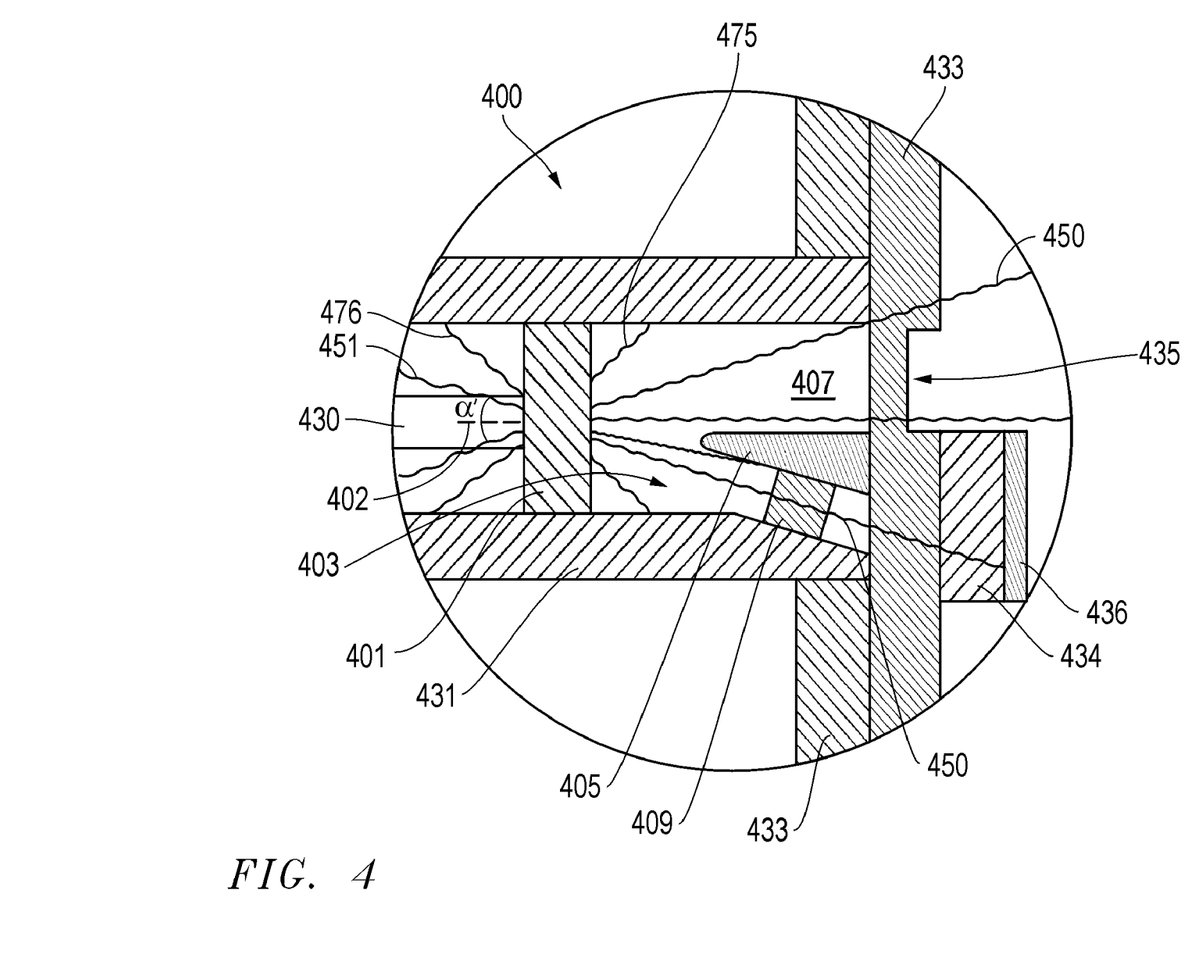
FIG. 4 is an enlarged view of a portion of an alternate embodiment of an oilfield x-ray tool.

In alternate embodiments, a filter 409 may even be positioned in advance of the reference detector 134, 434 to mimic the attenuation that occurs in the material of the fluid line 150 itself. For example, where detected x-rays 250 traverse about 1 inch thickness of fluid line 150 wall material before detection by the measurement detector 177, the filter 409 may be about 1 inch of the same material as that of the fluid line 150. In this manner an improved baseline may be obtainable from the reference detector 134, 434. Regardless, detector shielding 136 is coupled to the reference detector 134, and the measurement detector 177 for that matter, to attenuate any x-rays 250 that remain.

Referring now to FIG. 3 a fracturing assembly 300 is depicted at an oilfield 301. The fracturing assembly 300 may be employed to direct a fracturing fluid 360 down a well 310 at pressures in excess of about 15,000 PSI. In this manner the fracturing fluid 360 may penetrate a subterranean production region 375 to form a fractured area 370. Access to hydrocarbons within the production region 375 may thus be enhanced. In order to reach the well 310, the fracturing fluid 360 may be directed through a fluid line 330 and to a wellhead 340 atop the well 310. A series of high pressure triplex or other pumps, a manifold and other equipment (not shown) may be disposed in advance of the fluid line 330 in order to drive the fracturing fluid 360 therethrough as described.

Density and other characteristics of the fracturing fluid 360 may be critical to the fracturing operation. Therefore, an embodiment of an oilfield fluid x-ray tool 100 as detailed above may be secured to the fluid line 330 and operated to detect and monitor characteristics of the fracturing fluid 360 as it is added to the well 310. As shown in FIG. 3, constituents of the fracturing fluid 360 may include a liquid and a proppant 365 which are combined at a mix tub 325 to achieve predetermined fracturing fluid characteristics. The proppant 365 may include sand, a ceramic material, bauxite, glass beads, or a salt. Regardless, the proper mixture of constituents may be critical to the fracturing operation. Therefore, the x-ray tool 100 may be employed to monitor the amount of proppant 365 that is provided to the well 310, for example, by monitoring the density of the fracturing fluid 360 as it passes by the tool 100 within the fluid line 330.

In the embodiment shown, the proppant 365 is combined with other constituents of the fracturing fluid 360 at the oilfield. However, in other embodiments, the fracturing fluid 360 may be provided to the oilfield with proppant 365 already therein. Nevertheless, pre-mixing of the fracturing fluid 360 may occur prior to delivery to the well 310. Regardless, employing the x-ray tool 100 in the manner indicated may be key to ensuring that the fracturing operation proceeds according to design with the proper mix of constituents in the fracturing fluid 360 and/or the proper total amount of proppant 365 delivered to the well 310. Furthermore, the x-ray tool 100 is compact enough to be safely hand-held and manually positioned as depicted in FIG. 3, due to target 101 and collimator 131 orientations such as those described above with reference to FIGS. 1 and 2.

Referring now to FIG. 4 the internals of an alternate embodiment of an oilfield x-ray tool 400 are depicted. As alluded to above, the tool 400 includes a filter 409 positioned in advance of a reference detector 434 to mimic the attenuation that occurs into the sidewalls of a fluid line such as the fluid lines 150, 330 of FIGS. 1 and 3. In this manner an improved baseline of x-ray detection data may be obtainable from the reference detector 434. Thus, a more accurate determination regarding characteristics of oilfield fluid through the fluid line may be made. That is, attenuation of x-rays 450 unrelated to the oilfield fluid may be substantially accounted for in the readings obtained by the reference detector. Therefore, when the information from a detection mechanism at the other side of the fluid line is analyzed in comparison to information from the reference detector 434, a more accurate determination of characteristics of the fluid within the fluid line may be made.

Continuing with reference to FIG. 4, the x-ray tool 400 operates similar to that of FIGS. 1 and 2 described hereinabove. Namely, a target 401 is positioned within a collimator 431 to receive and block an electron beam 402 in x-ray tube 430. The striking of the electron beam 402 against the target 401 leads to the generation of x-rays 450, 451, 475, 476 that are collimated by the collimator 431. With respect to x-rays 451 falling within the angle α', a certain amount of shielding may be provided at the opposite end of the x-ray tube 430 as detailed above with respect to FIG. 1. However, the amount of shielding required in order to render the x-ray tool 400 safe for manual use is minimal.

As with the embodiment of FIGS. 1 and 2, the collimator 431 and target 401 of FIG. 4 are oriented such that a significant amount of the x-rays 475, 476 are attenuated by the collimator 431 before leaving the area. Other channeled x-rays 451 directed back in the direction of the electron beam 402 are shielded as described above. However, the channeled x-rays 450 directed away from the x-ray tool 400 may be subdivided by a collimating splitter 405 into separate reference detector 403 and fluid line 407 channels. The appropriately shaped collimating splitter 405 of collimating material may be disposed within the collimator 431 between the target 401 and support plates 433 at the outlet 435 of the tool 400. As shown, the positioning of the collimating splitter 405 may provide the indicated channels 403, 407. The fluid line channel 407 may be directed at a fluid line for evaluating characteristics of an oilfield fluid therein as in the above described embodiments. Alternatively, the reference detector channel 403 may lead through the above described filter 409 and to the reference detector 434. A reference detector shield 436 may be secured thereto to ensure the safety of the tool 400 during operation for nearby users.

Figure 5:
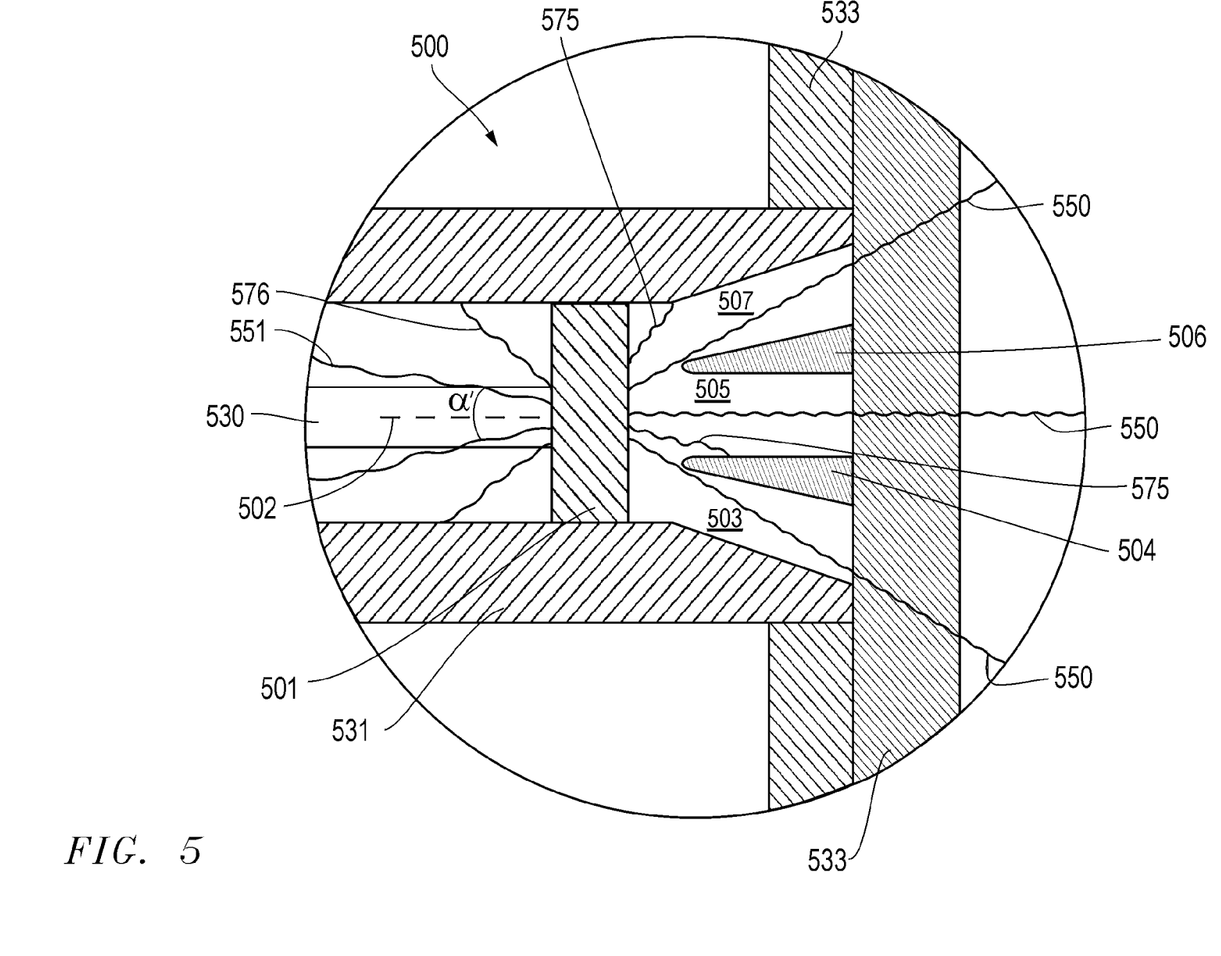
FIG. 5 is an enlarged view of a portion of yet another embodiment of an oilfield x-ray tool.

Referring now to FIG. 5, internals of another alternate embodiment of an oilfield x-ray tool 500 are depicted. In this embodiment a target 501 is again positioned within a collimator 531 to receive and block an electron beam 502 in x-ray tube 530. The striking of the electron beam 502 against the target 501 leads to the generation of x-rays 550, 551, 575, 576 that are collimated by the collimator 531. Again, as detailed above with respect to FIGS. 2 and 4, a certain amount of shielding may be provided at the opposite end of the x-ray tube 530 for attenuation of x-rays 551 falling within the angle α'.

In the embodiment of FIG. 5, channeled x-rays 550, 575 are emitted from the target in a direction away from the x-ray tube 530. Of these, a certain amount may be diverted or channeled by multiple collimating splitters 504, 506. That is, appropriately shaped collimating splitters 504, 506 of collimating material may be disposed within the collimator 531 between the target 501 and support plates 533. As shown in FIG. 5, the positioning of the collimating splitters 504, 506 may provide channels 503, 505, 507 for transmission of x-rays 550 across a fluid line similar to embodiments described above. In this manner, multiple detections of x-rays 550 may be made at the opposite side of the fluid line. With multiple data sets available relative to an oilfield fluid through such a fluid line, a variety of analysis may be undergone. For example, information obtained as a result of the multiple detections may be averaged to ensure a representative cross-section of fluid characteristic information is provided. Alternatively, the multiple detections may be compared with one another to provide phase fraction information about the fluid (e.g. liquid versus solid constituent information).

In another alternate embodiment employing an x-ray tool 500 such as that of FIG. 5, different detections corresponding to different channels 503, 505, 507 may be taken from across different locations of a fluid line or from across different fluid lines altogether. For example, detections may be taken from across a fluid line prior to and subsequent to addition of a proppant to a fracturing fluid for a fracturing application. Alternatively, one detection may be taken from across one fluid line delivering mud to a well during a drilling application and another detection taken from across a different fluid line returning mud from the well during the same drilling application.

Regardless of the particular embodiment employed, those detailed herein provide an effective means by which to obtain information as to an oilfield fluid characteristic, density or otherwise, in a non-radioactive manner. Thus, hazards to the user are substantially reduced. Furthermore, the x-ray tools described may employ configurations that significantly reduce the overall weight thereof by eliminating most of the x-ray shielding otherwise required for manual use of conventional x-ray tools. As a result, an x-ray tool of improved mobility may be provided.

The preceding description has been presented with reference to presently preferred embodiments. Persons skilled in the art and technology to which these embodiments pertain will appreciate that alterations and changes in the described structures and methods of operation may be practiced without meaningfully departing from the principle, and scope of these embodiments. For example, embodiments are described herein primarily with reference to an oilfield fluid in the form of a fracturing fluid that is added to a well. However, other oilfield fluids may be monitored with embodiments described herein, including oilfield fluids that are extracted from the same well such as produced hydrocarbons, circulating drilling mud, and others. Furthermore, the foregoing description should not be read as pertaining only to the precise structures described and shown in the accompanying drawings, but rather should be read as consistent with and as support for the following claims, which are to have their fullest and fairest scope.

We claim:

1. An x-ray tool for determining a characteristic of an oilfield fluid, the x-ray tool having a generator portion comprising:
    a housing;
    an x-ray tube disposed within said housing to direct an electron beam;
    a target at one end of the x-ray tube for receiving the electron beam and emitting x-rays; and
    a collimator about said target for collimating the x-rays, wherein said collimator and said target are of a unitary monolithic configuration.

2. The x-ray tool of claim 1 wherein the target end is a first end, the generator portion further comprising a shielding accommodated by said housing at a location adjacent a second end of said x-ray tube opposite the first end.

3. The x-ray tool of claim 2 wherein the first end is grounded.

4. The x-ray tool of claim 2 wherein said shielding is of a material selected from a group consisting of lead, gold, and tungsten.

5. The x-ray tool of claim 1 wherein a portion of the x-rays are released from the collimator across multiple x-ray channels for multiple x-ray detections.

6. The x-ray tool of claim 5 wherein the multiple x-ray detections occur front across multiple oilfield fluid lines adjacent the generator portion.

7. The x-ray tool of claim 5 wherein the multiple x-ray detections occur from across a fluid line adjacent the generator portion to provide one of an average of data regarding the characteristic of the oilfield fluid in the fluid line and a phase fraction characteristic of the oilfield fluid in the fluid line.

8. The x-ray tool of claim 1 wherein the characteristic is one of density, solid fraction, physical state, and material composition.

9. The x-ray tool of claim 1 wherein said x-ray tube is positioned within a dielectric material of said housing said dielectric material space is one of sulfur space hexafluoride or transformer oil.

10. The x-ray tool of claim 1 wherein said collimator is of a material selected from a group consisting of lead, gold, and tungsten.

11. The x-ray tool of claim 1 wherein said tool comprises a hand-held, manually positionable tool.

12. The x-ray tool of claim 1 wherein portions of the x-rays are released from ends of the collimator over a range of between about 1° and about 10°.

13. The x-ray tool of claim 1 wherein said target is of a material selected from gold, nickel and copper.

14. An x-ray tool assembly for determining a characteristic of an oilfield fluid, the assembly comprising:
    a generator portion comprising:
    a housing;
    an x-ray tube disposed within said housing to direct an electron beam;
    a target at the end of said x-ray tube for receiving the electron beam and emitting x-rays; and
    a collimator about said target for directing a portion of the x-rays through a fluid line of the oilfield fluid, said collimator and said target being a unitary monolithic configuration;
    a detector portion for detecting the portion of the x-rays through the fluid line; and
    a cuff coupled to said generator portion and said detector portion, said cuff for securing said generator portion and said detector portion about the fluid line.

15. The x-ray tool assembly of claim 14 wherein the target end is a first end, the generator portion further comprising a shielding accommodated by said housing at a location adjacent a second end of said x-ray tube opposite the first end.

16. The x-ray tool assembly of claim 14 wherein the fluid line is of at least a 15,000 psi. rating, and the electron beam to be accelerated to between 100 keV and 400 keV.

17. The x-ray tool assembly of claim 14 wherein said generator portion further comprises a reference detector to detect a portion of the x-rays from said target apart from the fluid line.

18. The x-ray tool assembly of claim 17 further comprising a filter positioned between said target and said reference detector to mimic sidewalls of the fluid line.

19. The x-ray tool assembly of claim 14 wherein said detector portion is collimated.

20. The x-ray tool assembly of claim 14 wherein the oilfield fluid is one of a fracturing fluid, a cement slurry, and drilling mud.

21. The x-ray tool assembly of claim 14 wherein said assembly comprises a hand-held, manually positionable assembly.

22. A method of determining a characteristic of an oilfield fluid, the method comprising:
    providing an x-ray generator at a fluid line with the oilfield fluid therein;
    collimating x-rays from a target with a collimator thereabout and within the generator, said collimator and said target being a unitary monolithic configuration; and
    detecting a portion of the x-rays with a detection mechanism at a location of the fluid line opposite the generator.

23. The method of claim 22 further comprising analyzing data from the detection mechanism in light of pre-stored oilfield fluid data.

24. The method of claim 22 wherein the portion is a first portion, the method further comprising detecting a second portion of the x-rays from the target with a reference detector apart from the fluid line.

25. The method of claim 24 further comprising analyzing data from the detection mechanism in light of data from the reference detector.

26. The method of claim 24 further comprising employing data from the reference detector to adjust a level of x-rays emitted from the target.

27. The method of claim 22 wherein providing comprises providing an x-ray generator that is hand-held and manually positionable.

28. The x-ray tool of claim 27 wherein providing further comprises manually positioning the x-ray generator.

* * * * *